(12) United States Patent
Cerofolini et al.

(10) Patent No.: US 9,271,682 B2
(45) Date of Patent: Mar. 1, 2016

(54) INTRODUCTION OF AN OBJECT IN A BODY UNDER REAL TIME IMAGING VIA CORRELATION OF IMAGES OBTAINED BY DIFFERENT IMAGING APPARATUSES

(75) Inventors: Marino Cerofolini, Subbiano (IT); Barbara Greppi, Fiesole (IT)

(73) Assignee: Esaote, S.p.A., Milan (IT)

( * ) Notice: Subject to any disclaimer, the term of this patent is extended or adjusted under 35 U.S.C. 154(b) by 358 days.

(21) Appl. No.: 13/176,136

(22) Filed: Jul. 5, 2011

(65) Prior Publication Data
US 2012/0010501 A1 Jan. 12, 2012

(30) Foreign Application Priority Data

Jul. 7, 2010 (IT) .............................. GE2010A0076

(51) Int. Cl.
| | |
|---|---|
| A61B 6/00 | (2006.01) |
| A61B 8/00 | (2006.01) |
| A61B 6/03 | (2006.01) |
| A61B 5/055 | (2006.01) |
| A61B 8/08 | (2006.01) |
| G06T 7/20 | (2006.01) |
| A61B 8/06 | (2006.01) |

(52) U.S. Cl.
CPC ................. *A61B 6/032* (2013.01); *A61B 5/055* (2013.01); *A61B 6/466* (2013.01); *A61B 6/503* (2013.01); *A61B 6/5247* (2013.01); *A61B 8/08* (2013.01); *A61B 8/4263* (2013.01); *A61B 8/5238* (2013.01); *G06T 7/2033* (2013.01); *A61B 6/4441* (2013.01); *A61B 8/065* (2013.01); *A61B 8/4245* (2013.01); *G06T 2207/10081* (2013.01); *G06T 2207/10124* (2013.01); *G06T 2207/10132* (2013.01); *G06T 2207/30048* (2013.01); *G06T 2207/30052* (2013.01)

(58) Field of Classification Search
CPC ..................................................... A61B 8/5238
See application file for complete search history.

(56) References Cited

U.S. PATENT DOCUMENTS

| | | | |
|---|---|---|---|
| 2007/0038084 A1* | 2/2007 | Burla et al. .................... | 600/437 |
| 2008/0146919 A1 | 6/2008 | Camus | |
| 2008/0298660 A1 | 12/2008 | Yamagata | |
| 2009/0036775 A1* | 2/2009 | Ikuma et al. .................. | 600/443 |
| 2009/0326373 A1 | 12/2009 | Boese | |
| 2010/0016709 A1* | 1/2010 | Gilboa et al. ................. | 600/424 |
| 2010/0063400 A1 | 3/2010 | Hall | |
| 2010/0114308 A1 | 5/2010 | Maschke | |

(Continued)

FOREIGN PATENT DOCUMENTS

| | | |
|---|---|---|
| EA | 1 623 674 A1 | 2/2006 |
| WO | WO 2010/064348 A1 | 6/2010 |

OTHER PUBLICATIONS

European Search Report from Ep 11172273.12 dated Aug. 1, 2011.

(Continued)

*Primary Examiner* — Amanda Lauritzen Moher
*Assistant Examiner* — Serkan Ankar
(74) *Attorney, Agent, or Firm* — Woodard, Emhardt, Moriarty, McNett & Henry LLP

(57) ABSTRACT

An imaging system and method are disclosed for monitoring a body. The system is constructed and arranged such that the method of use includes the acquisition of a first image and the acquisition of a second image. In the exemplary embodiment the first image is a volumetric three-dimensional image and the second image is a two-dimensional image.

22 Claims, 7 Drawing Sheets

(56) References Cited

U.S. PATENT DOCUMENTS

| | | | |
|---|---|---|---|
| 2010/0172567 A1* | 7/2010 | Prokoski | A61B 5/0064 382/132 |
| 2010/0198346 A1* | 8/2010 | Keogh et al. | 623/2.11 |
| 2010/0239150 A1 | 9/2010 | Ishikawa et al. | |

OTHER PUBLICATIONS

Huang et al., Dynamic 2D Ultrasound and 3D CT Image Registration of the Beating Heart, IEEE Transactions on medical Imaging, IEEE Service Center, Piscatway, NJ vol. 28, No. 8, Aug. 1, 2009, pp. 1179-1189 XP011249697.

* cited by examiner

INTRODUCTION OF AN OBJECT IN A BODY UNDER REAL TIME IMAGING VIA CORRELATION OF IMAGES OBTAINED BY DIFFERENT IMAGING APPARATUSES

REFERENCE TO RELATED APPLICATIONS

This application claims the foreign benefit of Italy Patent Application No. GE2010A000076, filed Jul. 7, 2010, which is hereby incorporated by reference in its entirety.

BACKGROUND TO THE INVENTION

The present invention generally relates to an imaging method for monitoring a body under examination, as well as the apparatus for performing such method.

Currently used monitoring imaging methods are based on the use of apparatuses acquiring high resolution images, mainly volumetric images, in order to have a better and more detailed picture of the body under examination.

Such apparatuses, such as for example CAT, MRI, Fluorangiography, besides generally having a large size and consequently causing drawbacks related to the fact of being cumbersome and to unnecessary costs, they provide a great amount of image data, whose processing is time-consuming and makes impossible to perform imaging sessions in real-time. This drawback is particularly serious when imaging has not only diagnostic purposes but when its further aim is the auxiliary monitoring during operations on the patient.

The need of real-time imaging for assisting operations further increases when the anatomical district or the organ to be monitored change over time or move, such as for example the heart.

In particular the percutaneous introduction of metallic objects either for diagnostic, surgery or therapeutic aims into specific positions of an anatomical district has several drawbacks which need to be solved. The most relevant one resides in the fact that these objects are at least partly made by metal and influence the magnetic field of a standard type tracking system reducing the visibility and the chances for the operation to be successful.

One particular and important example relates to the positioning of cardiac valves. In this case the fact of monitoring the orientation of the valve while introducing it, is very critical for the success of the operation, since a wrong orientation can compromise the operation, making it necessary to replace the valve consequently increasing costs. Cardiac valves generally comprise metal material that affect, while moving the valves, the magnetic field used by standard tracking systems reducing the visibility and the chances for the operation to be successful.

The ideal imaging technique for selecting the type of valve and its relative positioning is Multislice CT due to its high spatial resolution. However, currently such technique, can be used only when planning the operation, for example in order to define the size of the valve, since it cannot be performed in real-time nor in a hemodynamic and/or heart surgery room (so called cathlab) during the operation.

Document EP 1 467 317 discloses a method and an apparatus for combining first and second image data of an object, according to which an ultrasound detector repeatedly generates the first image data of the object and the second image data of the object are generated separately by means of a CT an MR a PET or an x-ray apparatus. The second image data being three-dimensional image data of the object. A combination device combines the first and second image data. A tracker of the ultrasound probe being provided for tracking the position of the ultrasound probe and of the two dimensional data generated by the ultrasound probe. The tracking device is used as a reference coordinate system in relation to which first and second image data can be registered in order to register first and second image data for combination. A certain position of the ultrasound probe and thus of the slice or section plane along which the image data is collected can be thus related to an identical section plane or slice in the three-dimensional image data allowing reconstruction of the image along the slice or section plane by using the second image data instead of the first image data generated by the ultrasound probe.

This device and method uses standard tracking devices in which the position sensors of the ultrasound probe operate in a magnetic field. No arrangement is taken for avoiding magnetic field disturbance in case that the system is used in combination with operations for positioning at least partly metallic objects in the imaged anatomical district.

SUMMARY

Therefore, one aim of the present disclosure is to provide a monitoring system which, by means of relatively simple and inexpensive arrangements, allows a body or a part thereof under examination to be monitored by real-time imaging while maintaining a high image quality, without the need of an excessive computation performance by the equipment and allowing to be used without a loss in precision for monitoring the positioning of at least partly metallic objects in an anatomical region. Moreover such method should be highly versatile, that is several types of diagnostic examinations have to be performed by it, thus it is necessary for it to be able to acquire real-time images, in order to display the acquired images on a moment-by-moment basis.

The present disclosure relates to an imaging system and method for monitoring a body. In one embodiment, the system provides a first image acquisition means allowing a volumetric three-dimensional image to be acquired in combination with a second two-dimensional image acquisition means.

Further forms, objects, features, aspects, benefits, advantages, and embodiments of the present invention will become apparent from a detailed description and drawings provided herewith.

DESCRIPTION OF THE DRAWINGS

These and other characteristics and advantages of the present disclosure will be more clear from the following description of some embodiments shown in annexed drawings wherein.

DESCRIPTION OF THE PREFERRED EMBODIMENTS

Figure 1:
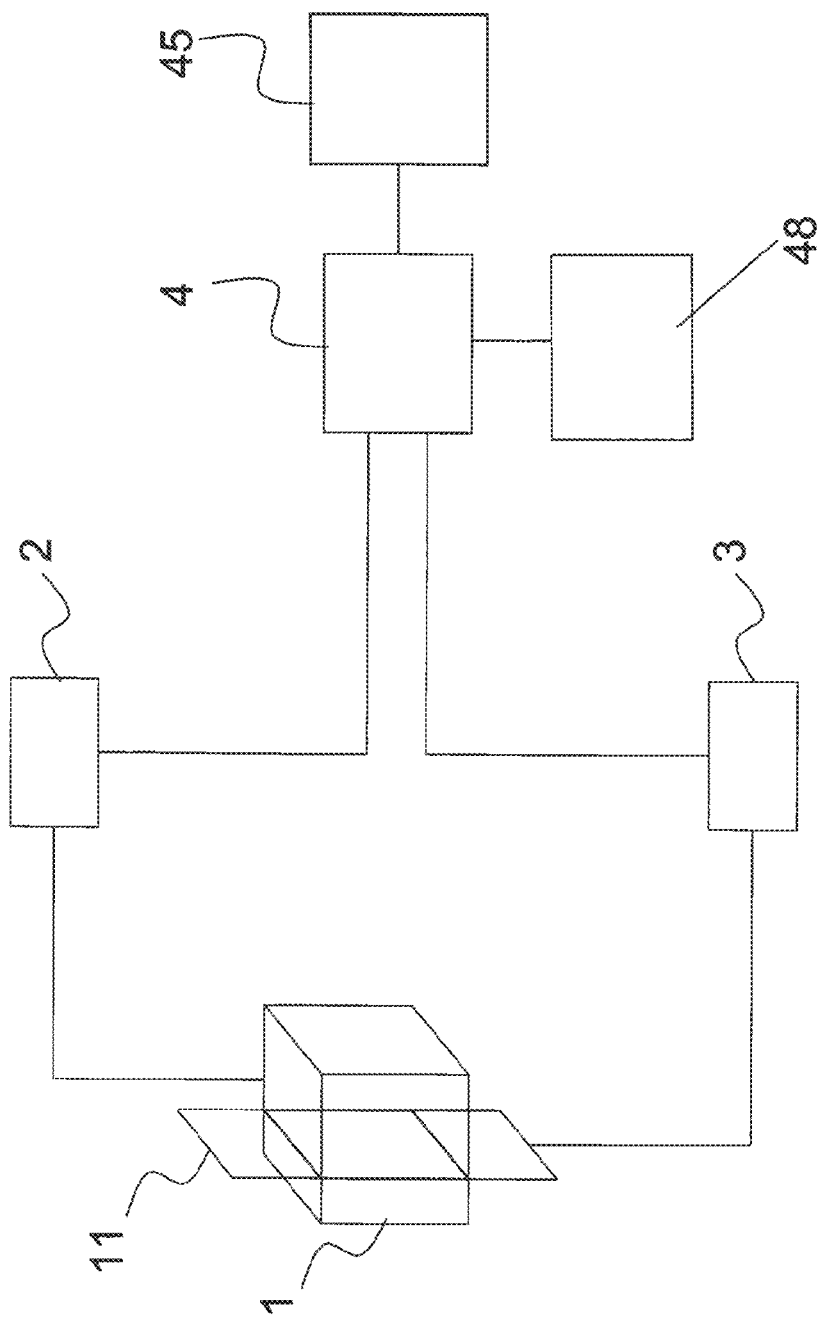
FIG. 1 schematically shows with function blocks the basic principles of the method and apparatus for tracking the ultrasound probe and registering the two dimensional image of the probe with the three dimensional images acquired at an earlier time and displaying an image corresponding to a two dimensional image reconstructed from the three dimensional image along the same slice or section plane as the image acquired by the ultrasound probe.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Except as specifically defined herein, the words/terms used in the claims is to only have its plain and ordinary meaning Such plain and ordinary meaning is inclusive of all consistent dictionary definitions from the most recently published Webster's dictionaries and Random House dictionaries.

One embodiment of the present disclosure achieves the above aims by providing an imaging method for the monitoring of an anatomical region during insertion of metallic objects or objects made at least partly of metal inside the region, which metallic objects disturb standard tracking systems, characterized in that it provides the following steps:

a) acquiring a three-dimensional image of a specific anatomical district (1) of the body under examination by a computed axial tomography device and storing said image data;

b) finding at least a reference point within said anatomical district;

c) acquiring a two-dimensional image along or at a first section slice or plane (11) of said anatomical district (1) passing by said at least one reference point by an ultrasound probe;

d) identifying said first section plane or slice (11) of the acquired two-dimensional image, within the stored three-dimensional image;

e) constructing a two-dimensional image (45) with data of the three-dimensional image falling along said first section slice or plane (11) which has been identified and corresponding to that of the acquired two-dimensional image;

f) moving said ultrasound probe towards at least a further section slice or plane (12) of said anatomical district (1) having a position and/or orientation different than that of said first section slice or plane (11) of step b);

g) tracking the displacement of said ultrasound probe for obtaining the image at said further section slice or plane (12);

h) identifying said further section slice or plane (12) within the stored three-dimensional image by using data related to the tracking of the displacement of said ultrasound probe;

i) constructing a two-dimensional image (46) with data of the three-dimensional image falling along said further section slice or plane (12) identified at step h);

j) displaying the two-dimensional image (46) obtained at step i) and keeping in place said ultrasound probe;

k) introducing said metallic object;

l) the section plane or the slice (12) along which the echographic image is acquired and along which the two-dimensional image is reconstructed from the three dimensional data being maintained fixed and corresponding to the section plane defined by anatomical markers, preferably at least three, while m) in the combined image deriving from the combination of the two dimensional image which has been reconstructed from the three-dimensional data with the two-dimensional echographic image, the contribution of the two-dimensional image reconstructed from the three-dimensional data corresponds to the representation of the anatomical structure and the contribution of the echographic image corresponds to the representation of the metallic object.

One application of the above method is in combination with the positioning of cardiac valves.

The present disclosure thus relates also to an imaging method for cardiologic monitoring and the anatomical district is the cardiac district, the metallic object is a cardiac valve to be introduced in the heart.

According to one embodiment, the two dimensional image reconstructed form the three dimensional image and the two dimensional echographic graphic image are displayed at the same time on a screen in two different regions of the screen which are one beside the other or one upper and one lower region or in the same region of the screen the images being displayed alternatively one to the other or the two images are displayed on the same region of the screen being superposed or combined one to the other.

According to an improvement of the method of the present disclosure, preferably after acquiring the three-dimensional image, it is possible to determine one or more reference points in order to facilitate the selection of the first section slice or plane from where the second image acquisition means has to start.

Such reference points are used for identifying within the volumetric image the plane or the slice along which the real-time image is acquired by ultrasound means.

Such reference points can be both external reference points and anatomical points inside the anatomical district, which can be easily recognized when acquiring images or which are recognized by using mathematical algorithms, such as for example trained neural networks, which process data of images obtained and stored during the acquisition. For example if the anatomical district is an area comprising the heart and/or an area immediately surrounding it, the coronary ostia are easy to be recognized due to their particular shape, or within the same area, in particular at the heart valves, it is possible to recognize the formation of calcium, whose presence can be easily detected due to the fact that calcium particles are bright if subjected to an ultrasound examination.

In the perspective of performing the method in real-time and of improving its performance velocity the use of these reference points allows the volume of the anatomical district under acquisition to be reduced, considering an area surrounding the reference points: thus 3 reference points are preferably used, in order to facilitate the choice of the first plane from which the displacement of the second acquisition means has to be measured, since there is only one plane passing by three not aligned points, consequently the plane from where the displacement tracking has to start is univocally determined.

The first acquisition means used for obtaining the three-dimensional image can be made using every available imaging means which is capable of generating such image data. Preferably this is a computed axial tomography device (CAT), while the second real-time acquisition means used for obtaining the two-dimensional image and used as the guide instrument inside the three-dimensional image is composed of an ultrasound system, in particular comprising an ultrasound probe.

Advantageously the displacement of the second means is tracked by using a sensor system, such as for example the Flock of Birds™ by Ascension Corporation or gMPS™ by Mediguide Inc.

According to an improvement of the method of the present disclosure the step for identifying the first section slice or plane of the image acquired by the second acquisition means within the three-dimensional image, is performed by using known mathematical algorithms such as for example the autocorrelation among data of the two-dimensional image and those of the three-dimensional image.

As already described above, once a two-dimensional image is acquired by the second imaging means, which two-dimensional image is along a section slice or plane passing by the selected reference points, the plane or the slice is recognized within the three-dimensional image by means of the reference points and of the fact that they must have the same relative positions as in the image acquired by said second imaging means. Such condition can be modified with different processing means, such as the autocorrelation or similar registration algorithms. Some examples are described in EP 1844440.

The method steps according to the present disclosure allow to overcome the problems of disturbance of the tracking sensors by means of at least partly metallic objects to be introduced in the anatomical region of the human body. Once the three-dimensional image is acquired the reference points which are important for the introduction of the cardiac valve are selected, such as for example the calcium particles accumulated on the valve to be replaced and here the first plane from where acquiring the two-dimensional image by the ultrasound probe is selected.

Then the ultrasound probe is moved towards the location where the valve is introduced until reaching it, the probe movement is registered and a two-dimensional high resolution image of the plane passing by the valve introduction location is obtained with data related to the corresponding plane belonging to the three-dimensional image.

Now the probe is kept fixed, and the cardiac valve begins to be inserted, whose movement is monitored by the ultrasound probe and when at the point of interest the cardiac valve is introduced by using the reference of the high resolution three-dimensional image, allowing the location to be seen in a better way allowing the valve to be properly introduced therein. Thus the effect of metal parts on position sensors is neutralized since the reference imaging is kept fixed, and therefore is independent of any change in the magnetic field caused by the metal material which may cause a wrong image to be selected.

Advantageously it is possible to enrich the high resolution image with the corresponding ultrasound image for example of the CFM and/or Doppler type to be overlapped or put beside it.

A further improvement of the method according to the present disclosure provides steps for monitoring that the echographic probe is held fixed in the position corresponding to the two dimensional image at the further section slice or plane on which the probe has been positioned in order to imagine the object to be inserted in the anatomic region the steps consisting in freezing a first echographic image taken at the further section plane or slice on which the probe has been positioned in order to imagine the object to be inserted in the anatomic region and displaying the frozen first image.

The further images acquired along the same said section plane or slice along which the frozen first image has been acquired being compared with the frozen image for detecting differences. A further step consists of signaling the detection of the differences. Each further image acquired along the further slice or section plane of the frozen first image are also displayed on the screen in a different screen region than the one in which the frozen first image is displayed or in the same region and in an alternate way to the frozen first image or superimposed to the frozen image.

According to a first variant, the comparison of the displayed image corresponding to the frozen first image with each of the images to be acquired along the same section plane or slice as the frozen first image is made by visual check.

According to a second variant the above comparison is made by processing of the image data relating to the frozen first image and to each of the images to be acquired along the same section plane or slice as the frozen first image with a comparison algorithm such as a correlation algorithm.

A further variant may comprise both the above said first and second variants allowing to carry out a visual comparison and a comparison based on correlation processing of the images.

According to still a further variant when the anatomical district to be imaged and in which the object has to be inserted is a moving organ, such as for example the heart, every one of the images acquired along the section plane or slice of the frozen first image including the frozen first image are synchronized by and ECG signal.

The above steps allow to control continuously that the probe is held fixed so that the slice or section plane along which the image is acquired is always the same during the entire duration of the operation and by signaling that a difference has been detected the user can immediately correct the position and orientation of the probe in order to bring the section plane or the slice along which the probe is currently acquiring images in coincidence with the section plane or slice along which the frozen first image has been acquired.

Still a further improvement may provide the generation of visual indicators of the displacements needed to correct orienting again the probe in order to bring the section plane or the slice along which the probe is currently acquiring images in coincidence with the section plane or slice along which the frozen first image has been acquired, when the comparison of the image acquired at a certain instant with the frozen first image has revealed that the section plane or slice along which the image has been acquired does not match with the section plane or slice at which the frozen first image has been acquired.

The indications are computed either from the data of the probe tracking unit and also from the differences of the section plane or slice along which the current image is acquired in relation to the section plane or slice along which the frozen first image has been taken.

The indications can consist in visual indications and/or acoustic indications. The visual indications can consist in arrows printed on the screen and which arrows show the direction of the displacement needed to correct the oprientation of the probe. The arrows may further indicate an approximate length of the displacement in the direction of the arrow, by having an arrow of different length which length is proportional to the length of the displacement and/or by having arrows of different thickness which thickness is proportional to the length of the displacement.

Acoustic signals may consist in simple beeps or tones or in vocal messages generated by a voice synthesizer.

The present disclosure relates also to a method for selecting and reconstructing images from a set of high resolution image data based on the previously described steps and in particular providing the acquisition of a high resolution volumetric image and storing it, acquisition of a low resolution two-dimensional image along or at a first section slice or plane of the high resolution volumetric image. Then the first section slice or plane of the acquired two-dimensional image is identified in real-time, within the stored volumetric image and a two-dimensional image is reconstructed with the data of the volumetric image falling along the first section plane or the first section slice identified and corresponding to that of the low resolution two-dimensional image acquired.

Similarly the present disclosure relates also to a device for performing the method described above, comprising a first three-dimensional image acquisition means and a second two-dimensional image acquisition means, a storage unit for storing image data acquired by the first and second image acquisition means, such storage means being connected to a registration and processing unit acquiring two-dimensional images and which associate them to three-dimensional images. Moreover there is provided a means for a system tracking the displacement of the second two-dimensional image acquisition means and a display unit for displaying three-dimensional and two-dimensional images acquired and/or processed by the registration and processing unit.

Advantageously the apparatus of the present disclosure provides the first acquisition means used for obtaining the three-dimensional image to be composed of a computed axial tomography device (CAT), while the second acquisition means used for obtaining the two-dimensional image to be an ultrasound system, in particular comprising an ultrasound probe. As an alternative or in combination with the CAT it is possible anyway to use also other acquisition methods such as MRI, fluoroangiography, PET, SPECT and the like.

According to an improvement the apparatus of the present disclosure provides the registration and processing unit to comprise processor means acting for executing a logic program intended for acquiring, processing and associating image data stored within the storage unit coming from the acquisition made by the first and second image acquisition means.

In addition the tracking of the displacement of the second acquisition means, in particular of the ultrasound probe, is performed by a means for a displacement tracking system composed of a sensor, or of a sensor system, which detects the probe and follows its displacement, storing the data inside the storage unit.

A variant embodiment of the apparatus of the present disclosure provides the processing and registration unit to be connected with a further diagnostic device for acquiring data of such device, process them and associate them to image data. According to a variant embodiment such processing and registration unit is connected to an electrocardiograph and it acquires and processes data coming from the first and second image acquisition means based on the different moments of the electrocardiogram graph.

As an alternative or in combination it is also possible to use a blood pressure monitor and/or any monitoring system for the movement of the structure under examination such as for example a device for measuring the breathing cycle such as a plethysmograph.

Data processed by the registration and processing unit are transmitted to the processing unit, which, according to a preferred embodiment, comprises a unit for identifying and displaying the reference points found within the volumetric three-dimensional image. The same display unit is generally composed of one or more display screens that contemporaneously display the several images and/or acquired data. Thus it is possible to contemporaneously display the three-dimensional image acquired by the first acquisition means, the one acquired by the second acquisition means as well as those processed by the registration and processing unit, such that the operator can have a complete overview of the body he/she is monitoring, composed of previously acquired images and or images processed in real-time.

According to a further improvement the imaging apparatus is provided with means for freezing an echographic image acquired at a certain instant and with means for comparing each image of a sequence of echographic images which has to be taken along the same section plane or slice as the frozen image at following times than the frozen first image. As used herein, a suitable means for freezing, as one example, would include a freeze-frame processor, an input and a display. When the input is active, the image flow is stopped and a fixed image is displayed. Image freezing as described herein is considered to be a well-known technique in image processing.

Signaling means may be provided which signals the occurrence of differences between the images of the sequence of images and the frozen first image. As used herein "signaling" means, or means for signaling, performs the function of signaling the occurrence of differences between the images. Means for signaling, as one example, would include a comparator combined into a signal emitter. This specific technology is considered to be well-known in the image-processing art.

Also an ECG unit is provided which collects ECG data and which triggers the image acquisitions according to the ECG signal in or to acquire images which are synchronized one with respect to the other by ECG signals. In this case when considering the cardiologic application synchronization means that each image is acquired during the same period of the cardiac cycle as measured by the ECG.

The frozen image and the images of the sequence of images which are taken along the same section plane or slice as the frozen image are displayed in different adjacent regions of the screen in order to allow a visual comparison of the images of the sequence of images with the frozen first image.

A processing unit may be provided which carry out the above comparison by running comparison program using a correlation algorithm.

The embodiments of the present disclosure relate also to other characteristics further improving the above monitoring apparatus and method and which are the subject of the dependent claims.

The apparatus comprises a first three-dimensional image acquisition means, particularly a computed axial tomograph 2, which acquires a volumetric image of an anatomical district 1 of the body under examination. Such image is sent to a registration and processing unit 4 which stores the three-dimensional image within the storage unit 41.

Moreover there is provided a second two-dimensional image acquisition means, an ultrasound device, in particular an ultrasound probe 3, which acquires a two-dimensional image of the anatomical district 1 at or along a first section slice or plane 11 thereof. The two-dimensional image is sent to the processing unit 4.

Image data obtained from the computed axial tomography 2 and from the ultrasound probe 3 are compared within a registration and processing sub-unit 42 within which there are provided processor means acting for executing a logic program such that the first section slice or plane 11 is identified and associated to the corresponding section slice or plane within the three-dimensional image acquired by the device 2.

Figure 2:
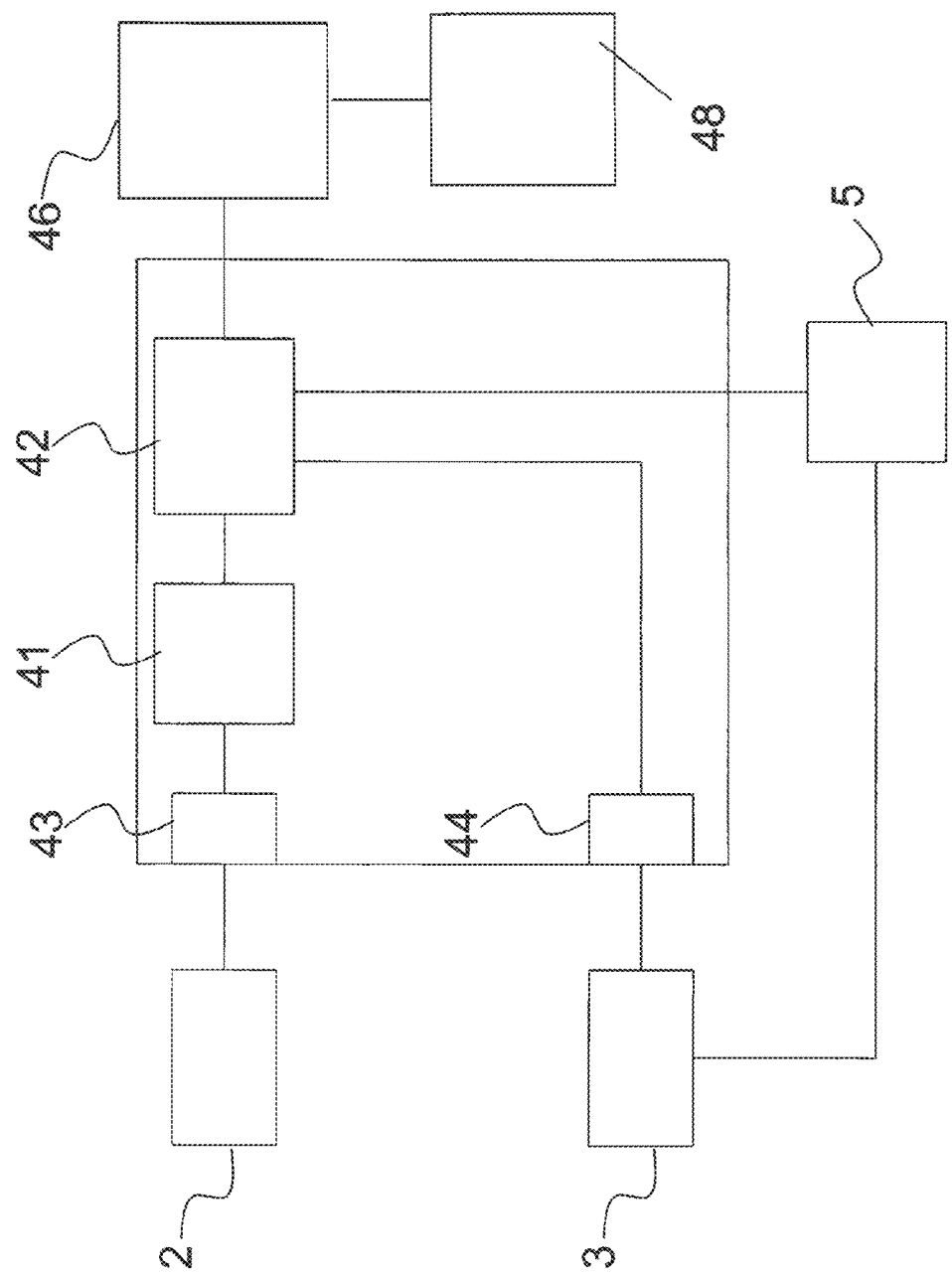
FIG. 2 schematically shows with function blocks an example of the registration and processing unit of the apparatus of FIG. 1.

Therefore the registration and processing unit, according to its preferred embodiment shown in FIG. 2, has an input channel 43 for image data from the computed axial tomography and an input channel 44 for image data from the ultrasound probe 3. Data from the channel 43 are stored within the storage unit 41, then are sent together with data from the channel 44 to the registration and processing sub-unit 42. Within the registration and processing sub-unit 42 all data will be processed such that the first section slice or plane 11 is identified and associated to the corresponding section slice or plane within the three-dimensional image acquired by the device 2.

Now the sub-unit 42 uses image data of the three-dimensional image acquired by the device 2 related to the section plane 11 identified within the three-dimensional image and it reconstructs a high resolution two-dimensional image 45 of the section slice or plane 11. One particular embodiment of the above method is disclosed for example in EP 1 467 317.

When the ultrasound probe 3 is moved towards a further section slice or plane 12 of the same anatomical district 1 having a position different than that of the first section slice or plane 11 previously selected, this displacement of the ultrasound probe 3 is tracked by a tracking system 5. The tracking system can be of any kind A preferred tracking system is composed of sensors registering the movements of the ultrasound probe 3 and sending data to the registration and processing unit 4, in particular to the registration and processing sub-unit 42.

The sub-unit 42, by the identification of the first plane 11 within the three-dimensional image which took place previously due to registration of the image data, reconstructs a new two-dimensional image 46 with the image data of the three-dimensional image falling along the new further plane 12 defined by the ultrasound probe 3 and identified with a corresponding plane belonging to the three-dimensional image, by simply moving on the three-dimensional image using the data related to the tracking of the displacement of the probe 3 which have been obtained by the sensor system 5.

Thus the probe 3, once the first plane 11 is identified within the three-dimensional image, is used as a guide instrument for moving inside the three-dimensional image.

A variant embodiment of the apparatus of the present disclosure provides a further rescaling unit which act for scaling the measurement of the displacement of the probe 3 to an equivalent measurement according to dimensions of the three-dimensional image, such that the plane 12 acquired by the probe 3 corresponds to a precise and univocal plane inside the three-dimensional image for the reconstruction of the high resolution two-dimensional image 46. Such unit can be integrated within the registration and processing sub-unit 42 or can belong to the tracking system 45.

The whole process is carried out in real-time mode, after having identified the first plane 11 within the three-dimensional image, the fact of tracking the probe displacement makes it possible to move along the three-dimensional image and to obtain a high resolution two-dimensional image since it is reconstructed from the volumetric image.

A variant embodiment of the method and of the apparatus of the present disclosure provides the volume of the anatomical district under acquisition to be reduced. One or more reference points are selected, preferably close to the part to be monitored and considering an area surrounding the reference points: preferably 3 reference points are used, in order to facilitate the choice of the first plane 11 where the measurement of the probe displacement has to start, since there is only one plane passing by three points, consequently the plane 11 is univocally defined.

A variant embodiment of the method of the present disclosure provides such method to be used in combination with another diagnostic method. This is particularly advantageous when monitoring moving organs or parts of the body, which change their condition depending on the moment when the registration occurs. For example in the case of cardiac monitoring it is possible to associate an electrocardiogram in combination with the computed axial tomography and with the ultrasound probe. It would be better to determine a specific time window within the graph of the electrocardiogram, preferably where the heart undergoes fewer changes, and the three-dimensional and the two-dimensional images are acquired periodically in the selected time window.

Figure 3:
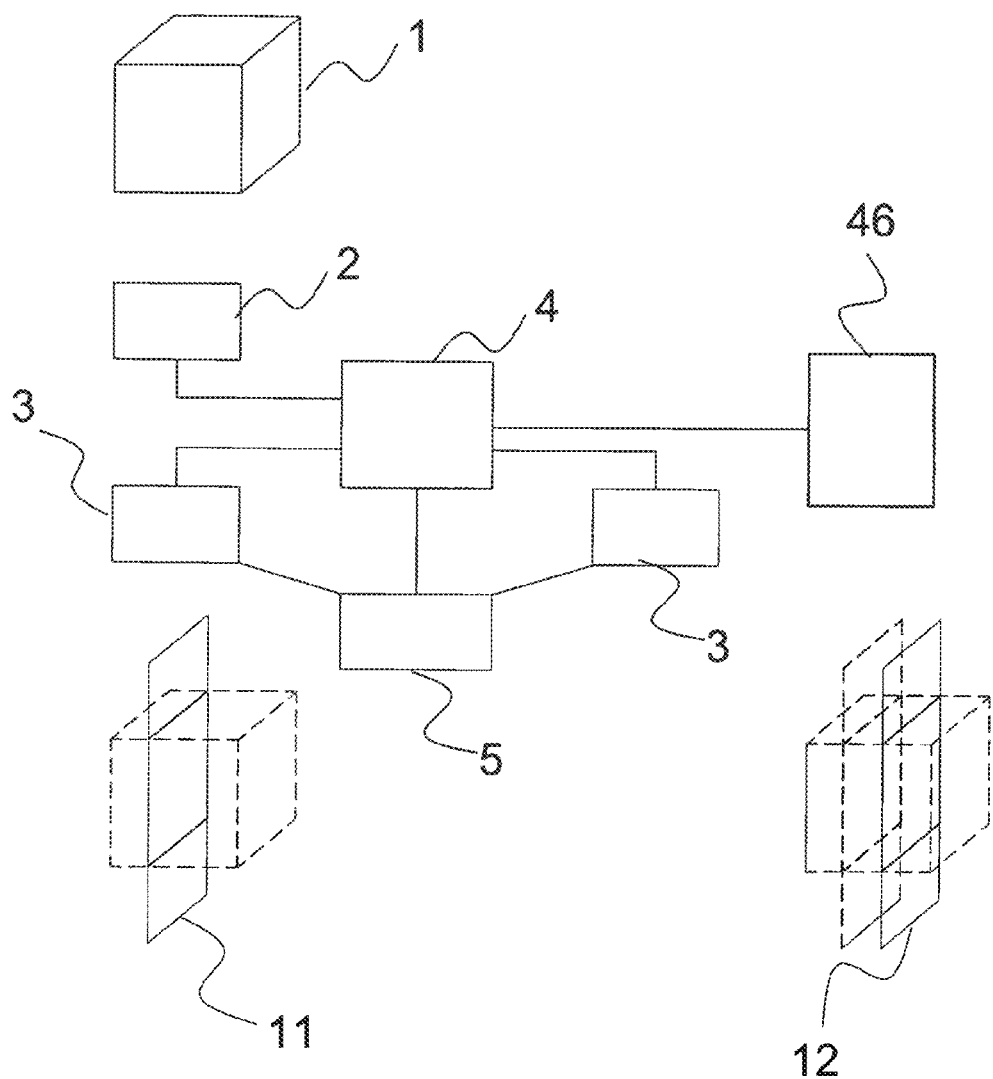
FIG. 3 schematically shows the several steps of the method of registering three-dimensional images with two dimensional images.

In particular FIG. 3 schematically shows the basic registration steps needed to carry out the method of the present disclosure. A first diagnostic image acquisition means 2 acquires a three-dimensional image of an anatomical district 1 of the body to be monitored, such image is stored within the registration and processing unit 4.

A second diagnostic image acquisition means acquires a two-dimensional image along a plane 11 of the anatomical district 1 and sends image data to the registration and processing unit 4. Such unit identifies the plane 11 within the stored three-dimensional image and in case it reconstructs a high resolution two-dimensional image by using the image data of the three-dimensional image which are relevant to the plane 11.

The second image acquisition means 3 is moved throughout the anatomical district 1 and it acquires a second two-dimensional image along a plane 12 having a position and/or orientation different than the first plane 11. The movement of the second acquisition means 3 is tracked by the tracking system which communicates to the registration and processing unit 4 the measurement of the displacement.

The registration and processing unit 4 identifies within the three-dimensional image the amount of the displacement of the second acquisition means 3 in order to reconstruct a high resolution two-dimensional image 46 using the image data of the three-dimensional image which are relevant to the plane 12.

It is possible to use one of the systems currently known on the market as the tracking system. A first tracking system is described in EP2147636.

As regards the identification of the plane or slice along which the starting image by the second acquisition means, particularly by an ultrasound system, and the three-dimensional image are acquired it is possible to use 2, preferably 3 reference points since 3 points univocally define a plane. All said reference points, or a part thereof, can be anatomical structures or anatomical markers. These have to be univocally present when acquiring the three-dimensional image by the first acquisition means and particularly by an apparatus for acquiring radiographic tomographic images.

When acquiring the two-dimensional image, the acquisition means are carried and oriented such to have all the reference points in the relative predetermined positions within the acquired image. The section slice or plane along which said two-dimensional image has been acquired is identified within said three-dimensional image as being the plane or slice where the reconstructed image provides a representation of the reference points identical within tolerances to those present in the three-dimensional image, which have been acquired by the second imaging means, in particular an ultrasound system. The fact of being identical can be defined by means of image comparison algorithms such as for example autocorrelation algorithms or the like.

Registration systems are known and are described in EP 1844440.

Figure 4:
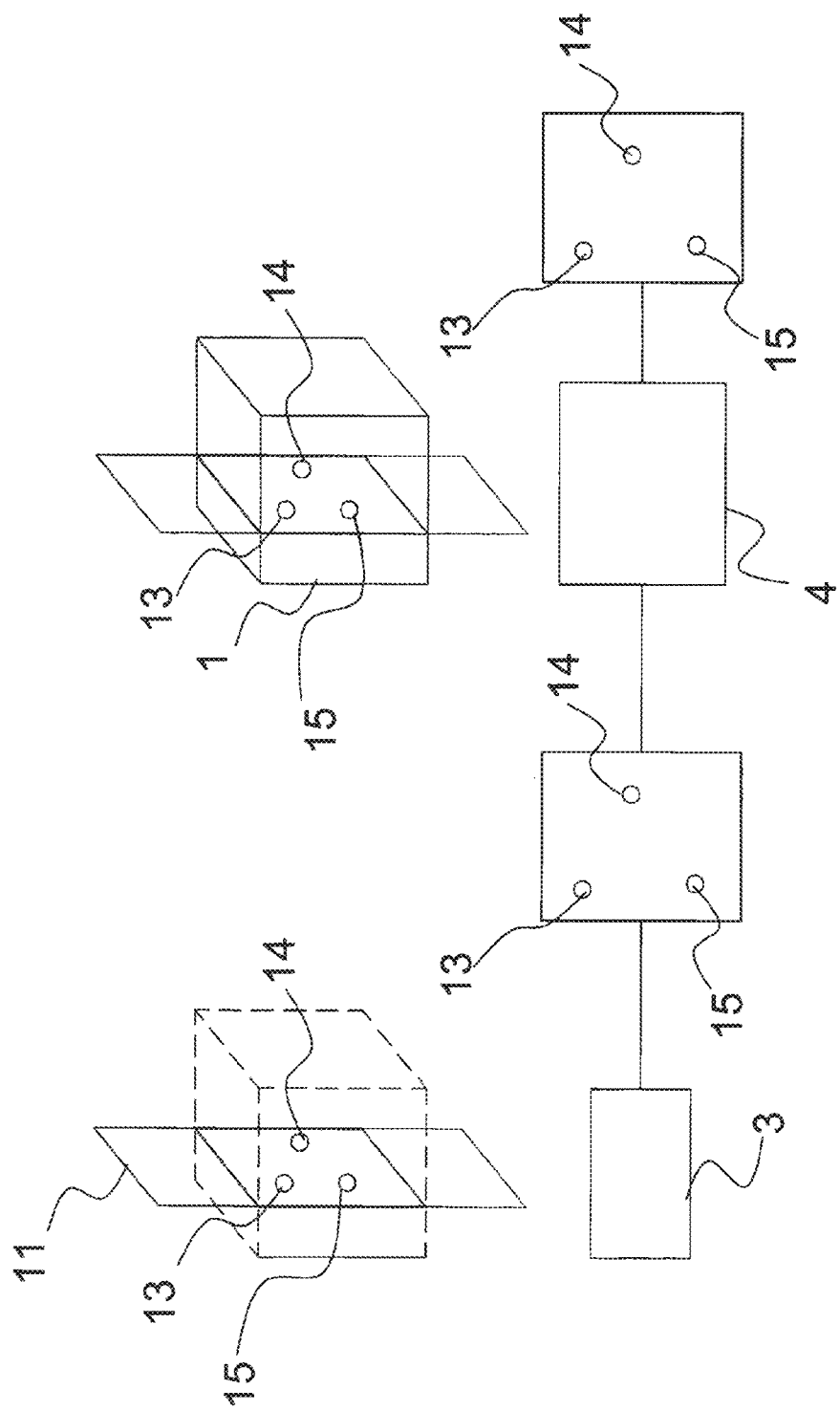
FIG. 4 schematically shows the steps of the starting phase of the method of the present disclosure.

In particular FIG. 4 schematically shows the method of the present disclosure according to a particular embodiment, according to which, after having acquired a three-dimensional image of the anatomical district 1 of the body under examination, by a first acquisition means, 3 reference points 13, 14 and 15 are found belonging to the anatomical district 1, preferably adjacent to an area of interest where the anatomical district 1 has to be monitored. Since there is only one plane passing by three points, such plane 11 is identified and a two-dimensional image is acquired along such plane 11 by the second acquisition means 3.

The two-dimensional image of the plane 11 acquired by the second acquisition means 3 is sent to the registration and processing unit 4, which acts for identifying such plane inside the three-dimensional image stored within the storage unit.

Once such plane 11 is identified within the three-dimensional image, the registration and processing unit 4 acts also for reconstructing the two-dimensional image 45 relevant to the plane 11, by using the image data of the three-dimensional image falling inside the plane, displaying by means of a high resolution image the three reference points 13, 14 and 15 and the surrounding area.

Now the monitoring of the body under examination is carried on by moving the second diagnostic image acquisition means 3 towards at least a further section slice or plane belonging to the same anatomical district 1 having a position and/or orientation different than that of the first section plane 11 which has been previously selected.

The displacement of the second diagnostic image acquisition means 3 is tracked such that, by the identification of the first plane 11 within the three-dimensional image which occurred previously, a new two-dimensional image is reconstructed with the image data of the three-dimensional image falling along the new further plane determined by the second acquisition means 3 and identified with a corresponding plane of the three-dimensional image, by simply moving on the three-dimensional image by using the data related to the tracking of the displacement of the second acquisition means.

These are the basic steps of the method according to the present disclosure. The complete method steps and the schematic structure of the device are described hereinafter with more detail with reference to FIG. 5.

Figure 5:
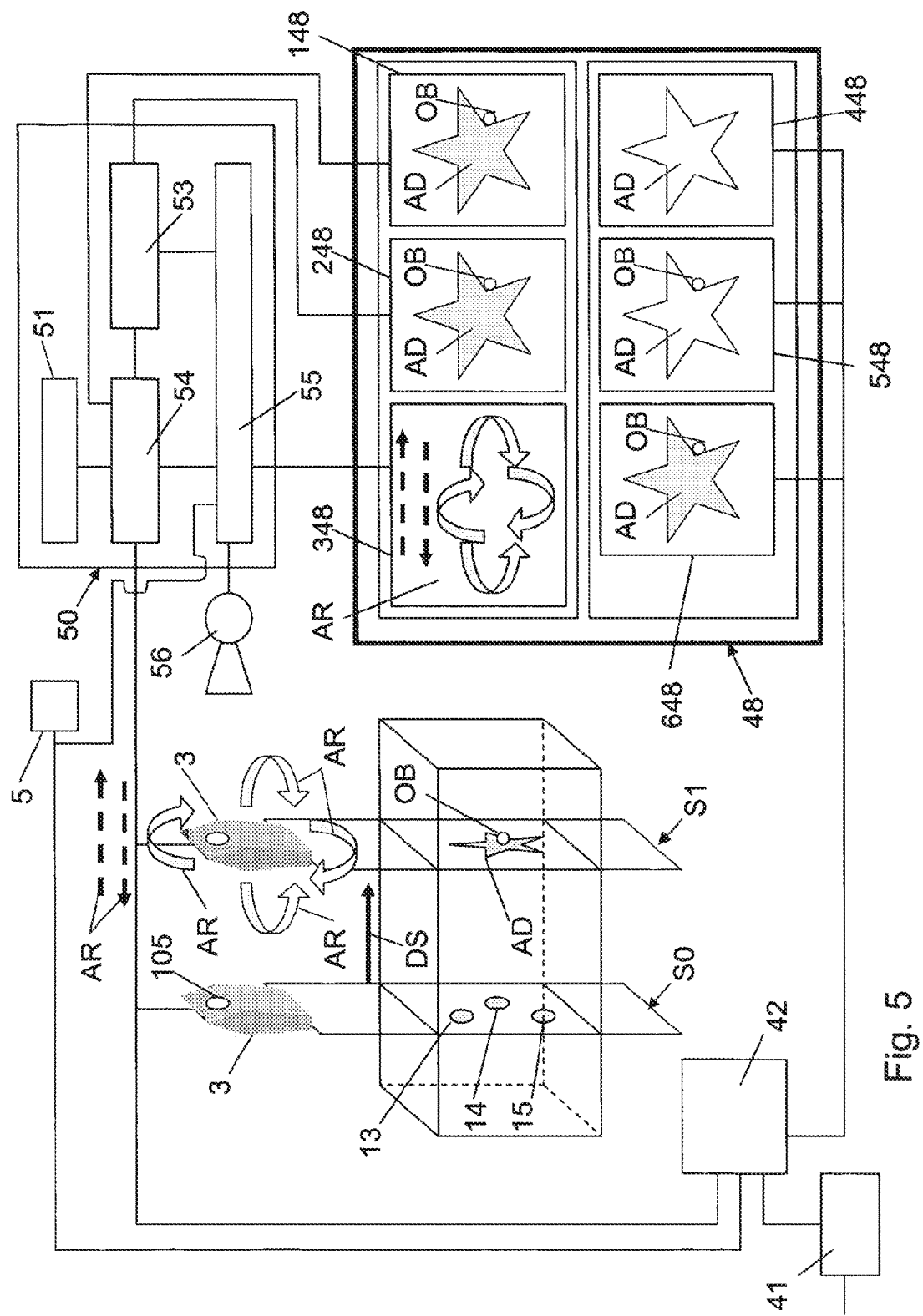
FIG. 5 schematically illustrates the method and apparatus according to the present disclosure.

In FIG. 5, slice S0 is the same slice as the slice represented in FIG. 4, which slice coincides with a plane containing the three reference points 13, 14, 15. As already explained in FIG. 4, the probe 3 carries a receiver 105 of the tracking system which receiver is sensed by the transmitter 5. At the beginning the probe 3 is displaced such as to generate a two dimensional image along a section plane or a slice coinciding with the plane containing the three reference points 13, 14, 15 and coinciding with the slice S0 in FIG. 5. This image data is sent to the registration and processing sub-unit 42 (see the more detailed block diagram representing the apparatus of FIG. 2). The registration and processing sub-unit 42 receives also the position and orientation data of the slice S0 relatively to the transmitter unit 5. The registration and processing unit can retrieve from the storage unit 41 the image data relative to the three-dimensional tomographic image acquired at an earlier time and can recostruct by means of the position and orientation data of the slice S0 a two dimensional image along the same section plane or slice as the slice S0 using the high resolution image data of the three dimensional image. Now a link has been generated between the slice and section plane along which the probe is acquiring a real time image and the image data of the three dimensional image along the same slice or section plane, so that for every image acquired by the probe 3 a two-dimensional image along the same plane or slice can be reconstructed using the image data of the three-dimensional image.

Once the registration link between ultrasound images and three-dimensional images has been generated, the method according to the disclosure provides the step of displacing the probe 3 as indicated by the arrow DS in FIG. 5 in order to generate a two-dimensional image along a slice or section plane S1 which contains the visual information data of the anatomical district, such as an organ, for example the heart which is needed for monitoring the positioning of the object in said anatomical district. In FIG. 5 the anatomical district AD is represented by a star and the inserted object to be positioned by a small circle indicated with OB.

The image along the slice S1 should be chosen such that it is the one giving the best morphological information for positioning the object OB.

According to the method of the present disclosure, once the two dimensional image along the slice S1 has been found, the probe 3 is held fixed in the position for generating images along the slice S1. A two dimensional image is reconstructed by means of the position and orientation information of the slice S1 from the three-dimensional data in the same way as for the first registration step using the slice S0. The reconstructed two dimensional image along the slice S1 is displayed for example in the area 448 of a screen 48. The corresponding ultrasound image can be combined such as superimposed to the reconstructed two dimensional image and displayed on a different region 548 of the screen. In the illustrated example the region 548 shows a result of a combination of the ultrasound and the reconstructed two dimensional image. The object OB derives from the ultrasound image while the anatomic image of the district AD is the reconstructed high resolution image of area 448. In a further region of the screen indicated by 648 the ultrasound image of probe 3 along slice S1 can be displayed.

Several different way of displaying the ultrasound images, reconstructed images and combination images are possible which may be for example using one and the same region and displaying the different images alternatively one to the other in a continuous sequence. The sequence may be also stopped or restarted by the user by means of a command signal, such as a button or a mouse click, or similar.

An alternative way is also displaying only the combination image of the reconstructed two-dimensional image and of the ultrasound image.

It has to be noticed that in the present FIG. 5, there is not shown the complete block diagram of the apparatus, but reference is made only to certain units which generate the relation to the more detailed description of the previous figures.

Once the steps are carried out, the probe is maintained fixed in order to generate a sequence of images along the same section plane or slice S1 while the object OB is introduced and positioned in the anatomic district AD. The probe being fixed, no data has to be generated by the tracking unit 5 so that the influence on the tracking system of the at least partly metallic object during its positioning are irrelevant for the imaging. The slice S1 remains fixed and also the two dimensional image reconstructed from the three dimensional image data long the slice S1. The object being a good reflector, normally a better reflector than biologic tissues do not need high resolution imaging and are imaged very good by the probe 3 in real time. By combining the ultrasound real time images of the sequence of images along the slice S1 with the reconstructed high-resolution image the anatomy of the site at which the object has to be positioned are best visible as well as the object itself and its displacements in time during positioning operations relative to the anatomy of the anatomic district AD. Some image data of the ultrasonic images relative to the anatomic region may also be used to complete the high resolution image reconstructed from the three-dimensional image data.

According to a further improvement of the above disclosed method and apparatus which can be provided in combination to the above disclosed method steps and apparatus as illustrated in FIG. 5, the present disclosure provides also for controlling that during the acquisition of the sequence of ultrasound images by means of the probe 3 along the chosen slice S1, the probe is effectively held fixed so that the slice of each of the acquired images of the sequence is always the same one for every image.

For sake of completeness FIG. 5 shows an embodiment which comprises also the units for carrying out the above mentioned control. It has to be noticed that these additional units and the additional method steps carried out by the units can also be omitted in the more generic embodiment of the present disclosure that has been disclosed in the above description.

According to the further improvement, the method provides steps for monitoring that the echographic probe is held fixed in the position corresponding to the two dimensional image at the further section slice or plane S1 on which the probe 3 has been positioned in order to imagine the object OB to be inserted in the anatomic region AD. The steps consist in freezing a first echographic image taken at the slice S1 and displaying the frozen first image. The further ultrasound images of the sequence of images acquired along the same slice S1 along which the frozen first image has been acquired are then compared with the frozen image for detecting differences. If differences are detected this condition is signalled.

According to a first embodiment, the comparison of the displayed image corresponding to the frozen first image with each of the images of the sequence of images acquired along the same slice S1 as the frozen first image is made by visual check.

The frozen first image along the slice S1 and the sequence of images acquired after the first one along the same slice S1 are displayed on a screen 48 in a different screen regions 148, 248.

Another way of displaying the images can be chosen such as for example alternatively displaying the frozen image and the currently acquired image of the sequence of images, or by superimposing the frozen image with each image of the sequence of images.

According to a second embodiment the above comparison is made by processing of the image data relating to the frozen first image and to each of the images of the sequence of images following the frozen first one and being taken along the same slice S1 as the frozen first image. Processing is carried out by a comparison unit 50, comprising a comparator unit 55 executing a program which carry out a correlation algorithm on the image data of the frozen image and on each image of the sequence of images.

Both the above embodiments can also be provided in combination allowing to carry out a visual comparison and a comparison based on correlation processing of the images.

According to still a further improvement when the anatomical district to be imaged and in which the object has to be inserted is a moving organ, such as for example the heart, every one of the images acquired along the section plane or slice of the freezed first image including the frozen first image are synchronized by and ECG signal.

The above steps allow to controll continuously that the probe is held always in a fixed position relatively to the imaged anatomical district, so that the slice or section plane along which the image is acquired is always the same during the entire duration of the operation. By signaling that a difference has been detected the user can immediately correct the position and orientation of the probe in order to bring the section plane or the slice along which the probe is currently acquiring images in coincidence with the section plane or slice along which frozen first image has been acquired.

In relation to the above signaling, still a further improvement may provide the generation of visual indicators of the displacements which are needed to correct orienting again the probe in order to bring the section plane or the slice along which the probe is currently acquiring images in coincidence with the section plane or slice along which the frozen first image has been acquired. The indicators are activated when the comparison of the image acquired at a certain instant with frozen first image has revealed that the section plane or slice along which the image has been acquired does not match with the section plane or slice at which the frozen first image has been acquired.

As it appears from FIG. 5, the indications are computed either from the data of the probe tracking unit and/or also from the differences of slice S1 along which the images of the sequence of images are acquired. In the example of FIG. 5 this processing is carried out by the comparator unit 55.

As illustrated in the example of FIG. 5, the indications can consist in visual indications and/or acoustic indications. The visual indications can consist in arrows AR displayed on the screen 48, in a certain region 348 of the screen which can be also a region dedicated only for such indications AR. The arrows AR show the direction of the displacement of the probe 3 needed to correct the orientation of the probe 3 in order to bring the scanning slice of the probe again in coincidence with the slice S1 along which the frozen image has been acquired and all the other images of the sequence of images has to be also acquired. The arrows AR may further indicate an approximate length of the displacement in the direction of the arrow, by having an arrow of different length which length is proportional to the length of the displacement and/or by having arrows of different thickness which thickness is proportional to the length of the displacement.

Acoustic signals may consist in simple beeps or tones or in vocal messages generated by a voice synthesizer indicating the kind of displacement such as rotation along the axis parallel to the scanning slice of the probe or along an axis perpendicular to the direction of propagation of the scanning beam and/or translation forward (left) backward (right) or other indications. The acoustic indications are diffused by a loudspeaker 56.

Relating to the apparatus means 54, 51 are provided for freezing an echographic image acquired at a certain instant and means for comparing each image of a sequence of echographic images which has to be taken along the same slice S1 as frozen image at following times than the frozen first image.

Signaling means 56, 148, 248, 348 may be provided which signals the occurrence of differences between the images of the sequence of images and frozen first image.

Also an ECG unit is provided which collects ECG data and which triggers the image acquisitions according to the ECG signal in or to acquire images which are synchronized one with respect to the other by ECG signals. In this case when considering the cardiologic application synchronization means that each image is acquired during the same period of the cardiac cycle as measured by the ECG. The ECG unit is not illustrated in the figures but its allocation in the block diagrams is evident for the skilled person The display screen 48 can be provided with different regions 148, 248 for displaying the frozen image and the images of the sequence of images taken along the same slice S1 as the frozen image. Means can also be provided for changing the display modus and displaying the frozen image and the images of the sequence of images in the same region in an alternate way or in a superimposed way of the frozen image and of each one of the images of the sequence of images.

A processing unit may be provided which carry out the above comparison by running comparison program using a correlation algorithm.

In FIG. 5 an example of a schematic embodiment is illustrated. The image data from the probe are sent to a storage and freezing unit 54 which is synchronized with a clock 51 for indexing each image with a time stamp which can be used as a parameter for calculating the memory address. The image to which the first time stamp of a sequence of time stamps is associated is frozen on the screen in the region 248. The images having the following time stamps are displayed one after the other in the correct time succession as their acquisition in the screen region 148. A visual comparison of the frozen image displayed in the region 248 with each of the images of the sequence of images displayed in the region 148 can be carried out.

In parallel as illustrated in FIG. 5 the image data of the frozen image and the image data of each of the images of the sequence of images are fed to a comparator unit 55, which executes a comparator program based on a correlation algorithm for determining each time an image of the sequence of images is acquired by the probe 3 if there is a difference of the image of the sequence of images relatively to the frozen one. If the difference occurs, a signaling action visual or acoustic can be emitted by printing messages on the screen 48 preferably in a dedicated area 348 or by emitting acoustic messages by means of a loudspeaker 56.

The comparator may operate by processing the images with a correlation algorithm. The comparator can also be connected to the transmitter 5 of the tracking system in order to receive information about the position and orientation of the probe 3 and thus of the scanning slice. This information is used to determine that the differences are caused by a movement of the probe 3 such that the scanning slice is not anymore coincident with the chosen slice S1 and to inform the user that a correction action has to be executed in order to bring the scanning slice of the probe 3 again in coincidence with the chosen slice S1. Indications for the correction actions to be taken by the user can be printed on screen such as the arrow AR in the dedicated region 348 of the screen 48 and/or can be also of the acoustic kind being diffused by a horn 56.

Figure 6:
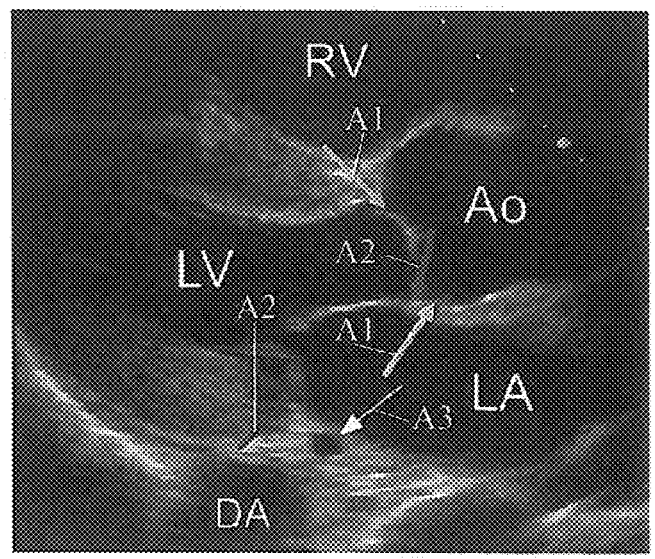
FIGS. 6 and 7 illustrate, respectively, one echographic image and the corresponding image constructed along the same slice from the three dimensional tomographic image data relative to a so called LAX of the Left ventricle taken with a transthoracic approach.
Figure 7:
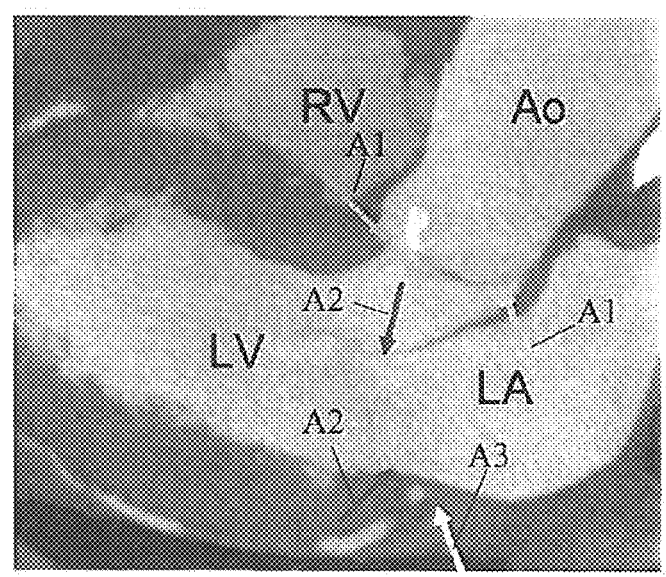

FIGS. 6 and 7 illustrate respectively one echographic image and the corresponding image constructed along the same slice from the three dimensional tomographic image data relative to a so called LAX of the Left ventricle taken with a transthoracic approach.

In FIGS. 6 and 7 the images are relative to a slice which renders visible the following anatomical details:
left ventricle indicated with LV
aorta indicated with Ao
left atrium indicated with LA
and descending Ao indicated with DA The echographic image is taken along a so called parasternal LAX and it is possible to identify the following fiducial points:
Indicated with A1 an insertion of anterior and posterior mitral leaflet on mitral annulus
Indicated with A2 insertion of non-coronary and left coronary leaflet on aortic annulus and indicated with A3 coronary sinus FIG. 7 illustrates the TAC image reconstructed from the three dimensional tomographic data along an image plane or slice which corresponds to the one along which the echographic image has been acquired.

The identity of the image planes or slices is determined using the above mentioned fiducial points identified by the arrows A1, A2 and A3. The tomographic two dimensional image corresponds to the echographic image, this means that the two images are along the same plane or slice of the object imaged when the fiducial points are all visible in the image and when the geometrical relative position of the points is identical in the echographic image and in the tomographic image. This can be determined with different mathematical techniques well known in the art one example of which is the cross correlation.

Starting from this registration image the position of the ultrasound probe when acquiring further images at different slices is tracked and the position of the slice of each following image is determined by computation using the position of the slice of the first registration image and the displacement data of the probe. This computation is carried out for determining the slice position and orientation along which each further image has to be reconstructed from the tomographic three dimensional image data, thus displacing the probe has the meaning of determining a displacement of the slice along which the image to be displayed has to be reconstructed. This image can be the echographic one taken at real time or the image can be the tomographic image reconstructed form the three dimensional image data at the same slice at which the echographic image has been acquired.

It is possible to display only the echographic image, only the tomographic image or both together in a side by side disposition or alternatively one to the other.

Figure 8:
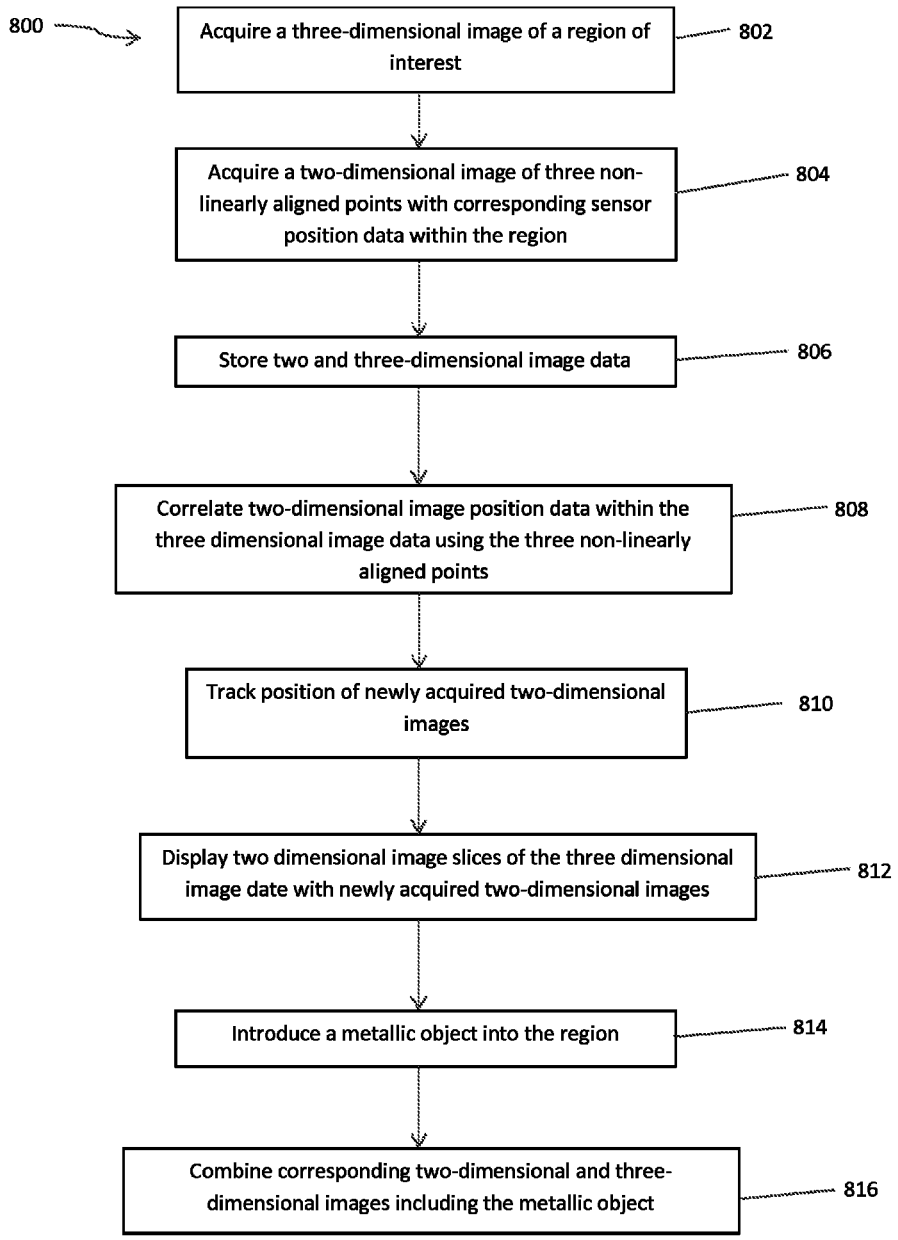
FIG. 8 illustrates a notional flowchart for the method and apparatus for tracking an ultrasound probe illustrated in FIG. 1.

FIG. 8 illustrates a notional flowchart of the method for the monitoring of an anatomical region during insertion of a metallic object inside the region described herein. The method constitutes the steps of acquiring a three dimensional image of a region of interest 802 and then acquiring a two dimensional image within the same region 800 of three non-linearly aligned points with corresponding position data of the image containing the three nonlinearly aligned points. Step 806 constitutes storing the two and three dimensional image data, such as with a storage unit.

Step 808 constitutes using a registration and processing unit to correlate two dimensional image data acquired in step 804 with the three dimensional image data acquired in step 802. The correlation includes determining a unique two dimensional image slice within the three dimensional image data corresponding with the two dimensional image.

Step 810 constitutes using a tracking unit to track the position of newly acquired two dimensional image(s). Step 812 constitutes the optional step of displaying two dimensional image slices of the three dimensional image data corresponding to the newly acquired two dimensional image(s).

Step 814 constitutes the optional step of introducing a metallic object within the region. Step 816 constitutes the optional step of combining two dimensional data with corresponding three dimensional data to form a composite image including the metallic object.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. It is also contemplated that structures and features embodied in the present examples can be altered, rearranged, substituted, deleted, duplicated, combined, or added to each other. The articles "the", "a" and "an" are not necessarily limited to mean only one, but rather are inclusive and open ended so as to include, optionally, multiple such elements.

What is claimed is:

1. An imaging method for the monitoring of an anatomical region during insertion of a metallic object inside the region, the method comprising:
   a) acquiring a three-dimensional image of a specific anatomical district of the body under examination by a computed axial tomography device and storing said three-dimensional image;
   b) finding three non-linearly aligned anatomical reference points within said anatomical district;
   c) acquiring a two-dimensional image along a first section slice of said anatomical district containing said three anatomical reference points by an ultrasound probe;
   d) correlating said three anatomical reference points of said two-dimensional image with said three-dimensional image and identifying said first section slice of the acquired two-dimensional image within the stored three-dimensional image;
   e) constructing a first two-dimensional image with data of the three-dimensional image falling along said first section slice and corresponding to that of the acquired two-dimensional image;
   f) moving said ultrasound probe towards a further section slice of said anatomical district having a position and/or orientation different than that of said first section slice;
   g) tracking the displacement of said ultrasound probe for obtaining the image at said further section slice;
   h) identifying said further section slice within the stored three-dimensional image by using data related to the tracking of the displacement of said ultrasound probe;
   i) constructing a second two-dimensional image with data of the three-dimensional image falling along said further section slice identified at step h);
   j) displaying the two-dimensional image obtained at step i) and keeping in place said ultrasound probe;
   k) introducing a metallic object;
   l) acquiring one or more further two-dimensional image along said further section slice, said image being acquired and generated in real time; and
   m) combining the second two-dimensional image which has been constructed from the three-dimensional data and the further two-dimensional images, and displaying the combination image, wherein the contribution of the first and second two-dimensional images reconstructed from the three-dimensional data corresponds to the representation of an anatomical structure and the contribution of the image corresponds to the representation of the metallic object.

2. The imaging method of claim 1, wherein the method is for cardiologic monitoring and the anatomical district is a cardiac district and the metallic object is a cardiac valve to be introduced in a heart, said further section slice along which the image is acquired and along which the two-dimensional image is reconstructed from the three dimensional data corresponds to the section plane of a left ventricle, the images being acquired in a transthoracic way, while in the combined image deriving from the combination of the two dimensional images which have been reconstructed from the three-dimensional data with the two-dimensional image, the contribution of the two-dimensional image reconstructed from the three-dimensional data corresponds to the representation of the anatomical structure and the contribution of the image corresponds to the representation of the cardiac valve.

3. The imaging method of claim 1, wherein the first and second two-dimensional images reconstructed from the three-dimensional image and the two-dimensional image are displayed at the same time on a screen in two different regions of the screen or in the same region of the screen with the images being displayed alternatively or superposed.

4. The imaging method of claim 1, wherein the image is acquired and generated in real time images.

5. The imaging method of claim 1, wherein step c) is performed by autocorrelation functions.

6. The imaging method of claim 1 further comprising reducing the volume of the stored three-dimensional image.

7. The imaging method of claim 1, wherein the method steps are provided in combination with a further diagnostic monitoring method.

8. The imaging method of claim 7, wherein said diagnostic monitoring method is an electrocardiogram and the acquisition of said three-dimensional image and of said two-dimensional images occurs at predetermined time intervals within the electrocardiogram.

9. The imaging method of claim 1, wherein the method monitors moving organs.

10. The imaging method of claim 1, wherein monitoring steps are provided for monitoring that the ultrasound probe is held fixed in the position corresponding to the two dimensional image at the further section slice, the monitoring steps comprising:
    freezing a first image taken at the further section slice;
    displaying the frozen first image;
        comparing further images acquired along the further section slice with the frozen first image for detecting differences between the actual scanning slice of the first image acquired and the further slice; and
    signaling the detection of the said differences.

11. The imaging method of claim 10, wherein each further images acquired along the further slice plane and the frozen first image are displayed on the screen in a different screen region or superposed and the comparison is made by visual comparation.

12. The imaging method of claim 10, in which the comparison is made by a comparison algorithm.

13. The imaging method of claim 10, wherein the images acquired along the section slice of the frozen first image are synchronized by an ECG signal.

14. The imaging method of claim 10, in which the signaling means comprises means for indicating the kind and the direction of the displacement of the probe in order to bring the scanning slice of the said probe in coincidence with the slice along which the frozen first image was acquired.

15. An imaging apparatus for monitoring a body comprising:
    a first three-dimensional diagnostic image acquisition sensor;
    a second two-dimensional image acquisition sensor;

a registration and processing unit having a memory and configured and arranged to correlate three non-linearly aligned anatomical reference points of two-dimensional images acquired by the second sensor with three-dimensional data acquired by the first sensor, wherein the images are stored in said memory;

a tracking system comprising a sensor and configured and arranged to track the displacement of said second two-dimensional image acquisition sensor;

a display configured and arranged for identifying and displaying a unique two-dimensional slice within said three-dimensional image data along with said three non-linearly aligned anatomical reference points defining said unique two-dimensional slice; and wherein the display is further configured and arranged for freezing an image acquired at a certain instant, comparing each image of a sequence of images which has to be taken along the same section plane as the frozen image, and signaling the occurrence of differences between the images of the sequence of images and the frozen image.

16. The imaging apparatus of claim 15, wherein said first diagnostic image acquisition sensor is a computed axial tomography device and said second image acquisition sensor is an ultrasound system.

17. The imaging apparatus of claim 15, wherein the registration and processing unit is programmed with a logic program for acquiring, processing and associating image data stored in said memory and acquired by said first image acquisition sensor and second image acquisition sensor.

18. The imaging apparatus of claim 15, wherein said registration and processing unit is configured and arranged for registering data acquired by at least a further diagnostic method as well as for associating said data to the image data.

19. The imaging apparatus of claim 15, wherein said display unit allows the image acquired by said first three-dimensional diagnostic image acquisition sensor, the image acquired from said second two-dimensional image acquisition sensor, and one or more images from said registration and processing unit to be contemporaneously displayed.

20. The imaging apparatus of claim 15, wherein the images are synchronized by ECG signals.

21. The imaging apparatus of claim 15, wherein the comparison is made visually by displaying on a screen the frozen image and in the corresponding succession each image of the sequence of images.

22. The imaging apparatus of claim 15, wherein the comparison is made by a processing unit using a correlation algorithm.

* * * * *